(12) United States Patent
Nakamura et al.

(10) Patent No.: US 6,457,858 B1
(45) Date of Patent: Oct. 1, 2002

(54) X-RAY APPARATUS AND METHOD

(75) Inventors: Kouji Nakamura, Kyoto; Katsuhiro Masuo, Kusorau; Tatsuya Araki, Ohmihachimann; Mikihiko Katoh, Kyoto, all of (JP)

(73) Assignee: Shimadzu Corporation, Kyoto (JP)

( * ) Notice: Subject to any disclaimer, the term of this patent is extended or adjusted under 35 U.S.C. 154(b) by 0 days.

(21) Appl. No.: 09/545,414

(22) Filed: Apr. 7, 2000

(30) Foreign Application Priority Data

Jun. 3, 1999 (JP) .......................................... 11-156362

(51) Int. Cl.$^7$ ................................................ H05G 1/02
(52) U.S. Cl. ........................ 378/196; 378/195; 378/197
(58) Field of Search ................................. 378/193, 196, 378/197, 195

(56) References Cited

U.S. PATENT DOCUMENTS

| | | | | |
|---|---|---|---|---|
| 5,050,202 A | * | 9/1991 | Yanome ..................... 378/167 |
| 5,386,453 A | * | 1/1995 | Harrawood et al. ......... 379/196 |
| 5,463,668 A | * | 10/1995 | Kagaya ..................... 378/98.2 |
| 5,497,408 A | * | 3/1996 | Kayser ........................ 378/196 |
| 5,682,414 A | * | 10/1997 | Saito ........................... 378/146 |
| 5,841,830 A | * | 11/1998 | Barni et al. ................... 378/15 |
| 5,870,450 A | * | 2/1999 | Khutoryansky et al. ..... 378/197 |
| 6,075,836 A | * | 6/2000 | Ning ............................ 378/17 |

OTHER PUBLICATIONS

Taber, Clarence Wilbur, Taber's Cycolpedic Medical Dictionary, 1997, 18$^{th}$ Ed., pp. 150 and 151.*
Taber, Clarence Wilbur, Taber's Cyclopedic Medical Dictionary, ed. 18, Pub. F.A. Davis Company, pp. 150–151.*

* cited by examiner

Primary Examiner—Robert H. Kim
Assistant Examiner—Chih Kao
(74) Attorney, Agent, or Firm—Rader, Fishman & Grauer PLLC

(57) ABSTRACT

During X-ray irradiation, a lever is operated to simultaneously move an imaging part and table in opposite directions from each other. A contrast medium's flow in an artery may be followed so that it is shown on a monitor. Relative speed of the table to X-ray imaging part can be adjusted by adjusting the amount of inclination of the lever.

12 Claims, 4 Drawing Sheets

X-RAY APPARATUS AND METHOD

BACKGROUND OF THE INVENTION

Description of the Related Art

FIG. 4 shows an apparatus for X-ray fluoroscopy, including an X-ray imaging system 60 and control system 59. The imaging system 60 has a table 40 for resting a person thereon. A X-ray tube 23 is disposed under the table 40. An X-ray imaging part includes an operation panel 25, a snap shot device 16, an image intensifier 15, and a TV camera 14.

The X-ray tube 23 and the X-ray imaging part are linked by a supporting column 24 and they travel as one united body. The X-ray tube 23 and the X-ray imaging part are movable in the Y axis direction 18, along the person's length, and also the X axis direction 17, along the person's width. These movements are carried out by manual operation or motor drive through operation of a handle 47. The X-ray imaging part is also designed to be movable in the Z axis direction 19, up and down with respect to the person. Enlargement fluoroscopy is carried out by adjusting the X-ray imaging part along the Z axis direction.

The operation panel 25 has various switches. Operation of some of these switches makes it possible to move the table 40, by motor drive in the Y axis direction 21 and the X axis direction 20, independently of the movement of the X-ray imaging part. Since the X-ray imaging part and table 40 are movable independently of each other, it is possible to place the center of the X-ray imaging part at a region of concern in the person. The X-ray imaging system 60 is also designed to incline by using switches on the operation panel 25 so that the person on the table 40 is held at a position between the horizontal position and the standing position.

The adjacent operation apparatus has a monitor 46 near the X-ray imaging system 60. When performing X-ray fluoroscopy using this apparatus, under irradiation of weak X-rays, an operator grasps the handle 47 to move the X-ray imaging system 60 first. The operator moves the table 40 and places the center of the X-ray imaging part at a region of concern of the person while watching an X-ray image on the monitor 46. Then, a radiography of the region of concern is carried out by pushing an imaging switch 48.

The control system 59 controls an X-ray high voltage generator 41 according to X-ray parameters preset ahead. When the X-ray high voltage generator 41 provides the X-ray tube 23 with high voltage, the X-ray tube 23 irradiates X-ray. The X-ray transmitted through the person is detected and also changed into a visible image by the image intensifier 15. The TV camera 14 converts the visible image output by the image intensifier 15 into video signals. An A/D converter 42 converts the video signals into digital signals. An image processor 43 carries out image processing of the digital signals to obtain a proper X-ray image. Output data of the image processor 43 are stored in the memory 45. The output data are also converted by a D/A converter 44 into analog signals and then provided to the monitor 46 and a TV monitor 26 of the control system 59 to show an X-ray image thereon.

In case that angiography of a relatively wide range, such as a blood vessel in a leg part, is carried out by using the above mentioned X-ray fluoroscopy apparatus, the X-ray imaging part is moved, thorough use of the handle 47, to track a blood stream (typically contrasted by a contrast medium). Radiography of the blood stream is carried out while tracking the blood stream by using the switch 48.

When angiography of a large person is carried out, since it is necessary to have the X-ray imaging part travel for about one meter, an X-ray imaging system which has the X-ray imaging part travel for a long distance is needed. However, the entire structure of the X-ray imaging system becomes very large when the X-ray imaging part is able to travel for a long distance.

In case of carrying out angiography of the whole body or a leg part, it is necessary to have the table 40 travel at velocity faster than the flow of blood; intermittent X-ray irradiation is repeated, having the table 40 move intermittently to get a target blood stream live image. However, this requires a high powered motor able to move the table to chase the X-ray imaging part, which is expensive.

SUMMARY OF THE INVENTION

It is therefore desirable to provide an apparatus for X-ray fluoroscopy and a method of angiography which carries out angiography over a wide range without making the apparatus large. It is also desirable to provide an apparatus for X-ray fluoroscopy and a method of angiography which make it possible to chase contrasted blood flow very easily.

DESCRIPTION OF THE PREFERRED EMBODIMENTS

Figure 1:
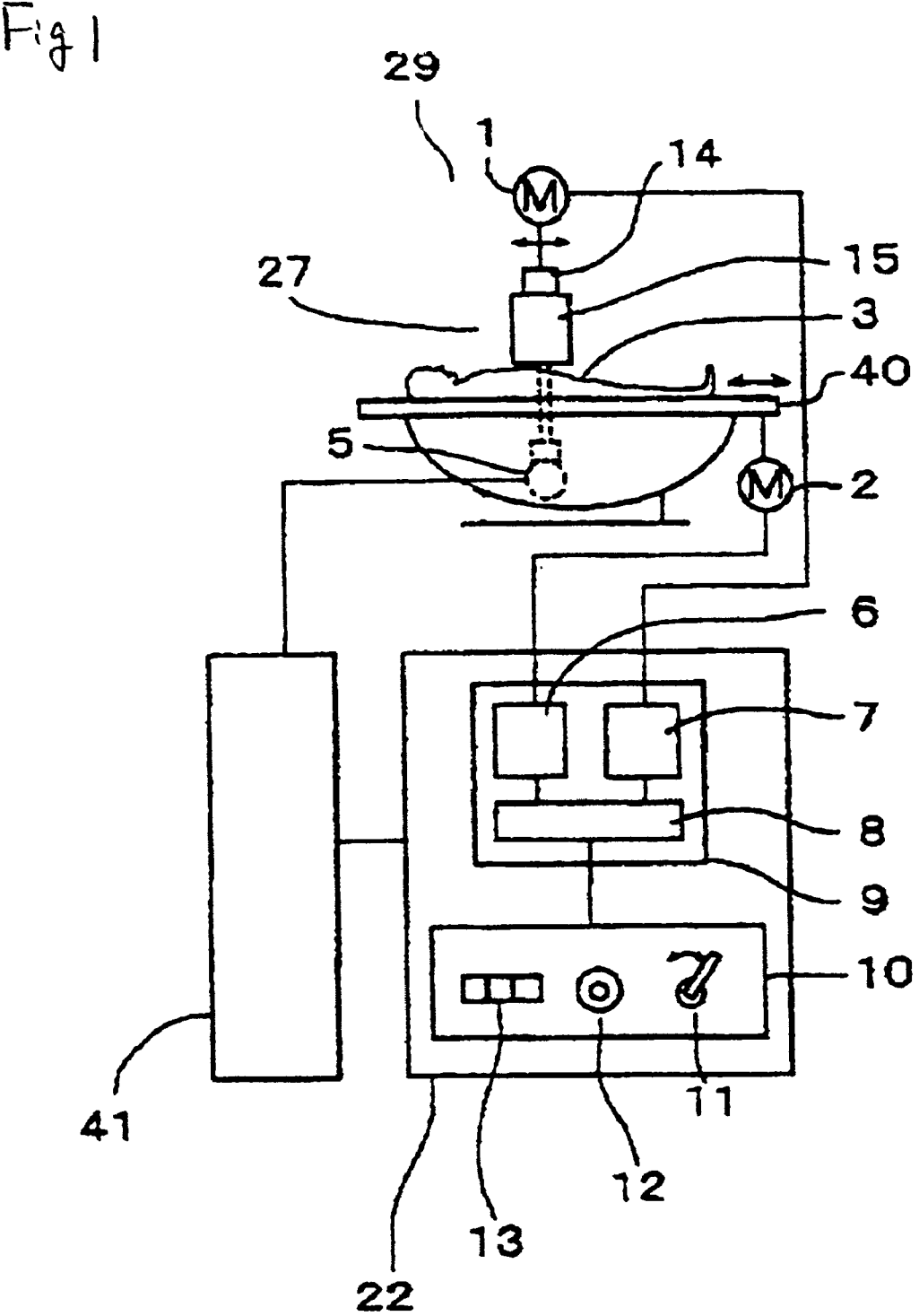
FIG. 1 is a schematic view of an apparatus for X-ray fluoroscopy in an embodiment of this invention.

FIG. 1 shows a schematic drawing of an apparatus for X-ray fluoroscopy of a preferred embodiment of the present invention. This apparatus comprises an X-ray imaging system 29, a X-ray high voltage generator 41, and control part 22. The X-ray imaging system 29 has a table 40 for resting a subject person 3 for examination thereon. A X-ray tube 5 is disposed under the table 40. The X-ray imaging part 27 has an image intensifier 15, a TV camera 14, and so on.

The X-ray tube 5 and the X-ray imaging part 27 are linked by an supporting column, not shown in FIG. 1, and they travel as one united body. The X-ray tube 5 and the X-ray imaging part 27 are movable about the length of the person 3 by a motor 1. The table 40 is moved along the width of the person 3 by a motor 2. These movements are carried out by a manual operation or a motor drive. The control part 22 has a controller 9 and a control panel 10. The control part 22 has a CPU 8, a table velocity control circuit 6, and an imaging part velocity control circuit 7. The control panel 10 has an image mode selection switch 13 for providing the controller 9 with command signals for image modes, an X-ray switch 12 for indicating irradiation of X-ray, and a lever 11 for providing instructions for controlling movement of the X-ray imaging part 27 and table 40.

The control part 22 is usually disposed with the X-ray imaging part 27 for operation near the person 3. The operator may inject a contrast medium into a vein or an artery and then carry out angiography near the person 3 operating the control panel 10 and so on.

Figure 2:
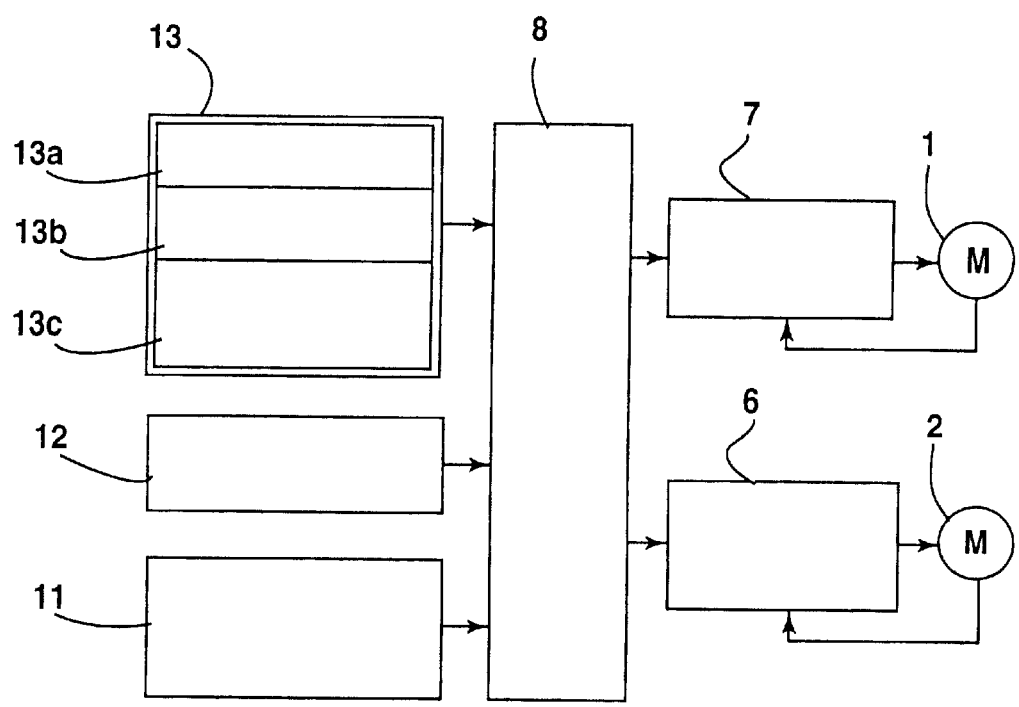
FIG. 2 is a block diagram of a controller for an X-ray imaging part and a table of the apparatus of X-ray fluoroscopy in an embodiment of this invention.
Figure 4:
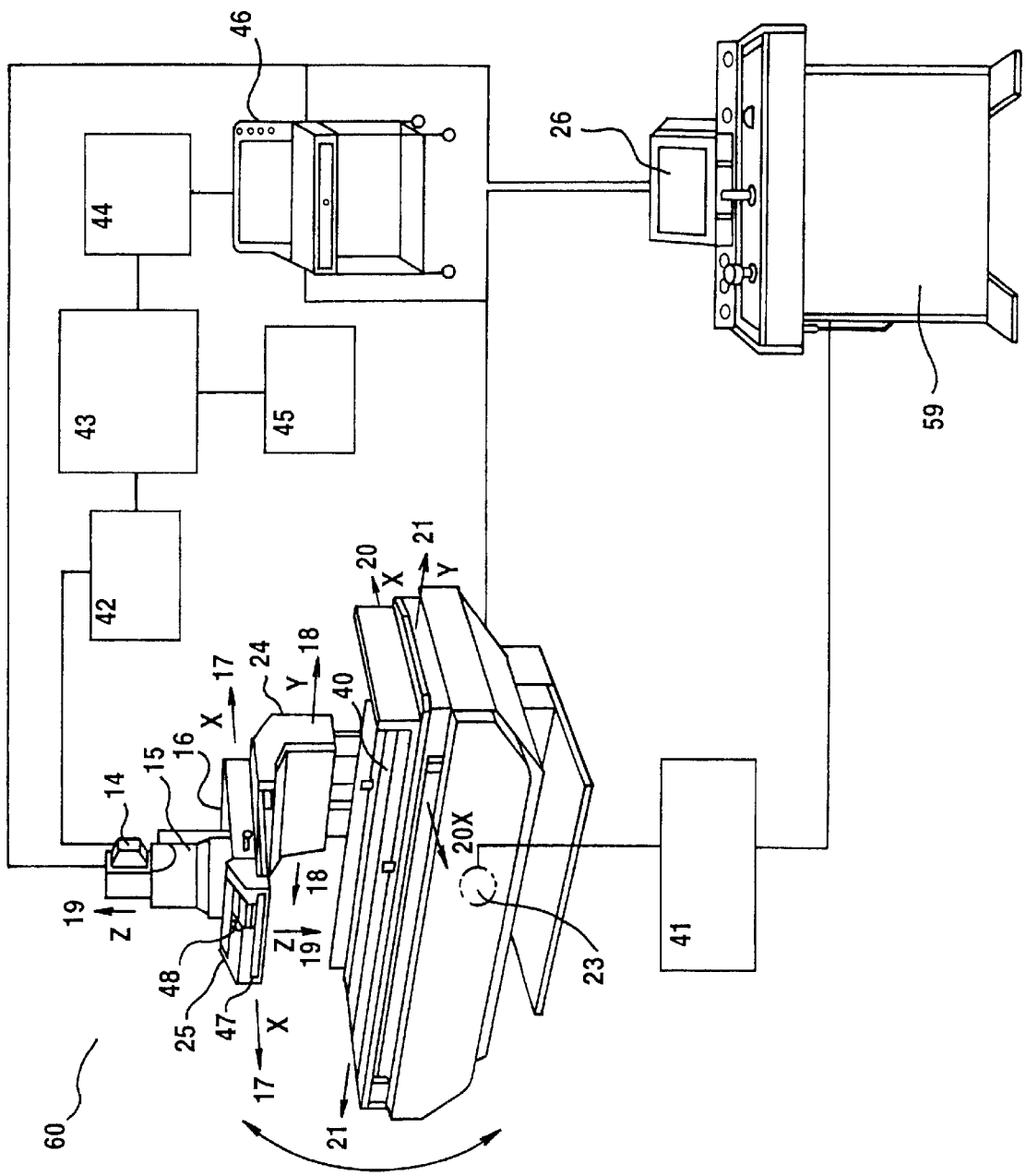
FIG. 4 is a schematic view of a related apparatus for X-ray fluoroscopy.

FIG. 2 shows a detailed block diagram of the control part 22. The imaging mode selection switch 13 on the control panel 10 of the control part 22 has a switch for selecting a normal mode 13a, a switch for selecting an imaging part moving mode 13b, and a switch for selecting an imaging part and table moving mode 13c. Only one mode is selected by selecting one of these three switches. The normal mode 13a allows the conventional method in which angiography is carried out, for example, using an operation handle (not shown in the FIG. 1) and moving the X-ray imaging part 27 or the table 40 as done in the device of FIG. 4. In the imaging part moving mode 13b, the controller 9 controls the motor to move the X-ray imaging part 27 in the longitudinal direction of the person 3, according to the operation of the lever 11.

In the imaging part and table moving mode 13c, the controller 9 controls the motor 1 and motor 2 to move the X-ray imaging part 27 and the table 40 in the opposite direction from each other, according to the operation of the lever 11. The controller 9 controls the motor 1 and motor 2 so that the direction of the inclination of the lever 11 corresponds to the direction of the movement of the X-ray imaging part 27 and also to the opposite direction of the movement of table 40. The lever 11 has a sensor for detecting an inclination from its neutral position. The sensor output is provided to the CPU 8. When the operator inclines the lever 11 in the left direction in FIG. 1, the CPU 8 controls the motor 1, through the imaging part velocity control circuit 7, to move the X-ray imaging part 27 in the left direction in FIG. 1 at the speed corresponding to the amount of inclination. The CPU 8 also controls the motor 2, through the table velocity control circuit 6, to move the table 40 in the right direction in FIG. 1 at the speed corresponding to the amount of inclination. The relation between the amount of inclination of the lever 11 and the speed is set so that the speed increases as the amount of inclination increases. The relation between them may be set so that the speed is in proportion to the amount of inclination of the lever 11.

Instead of the above embodiment, the CPU 8 may control the motor 2 to move the table 40 in the direction of inclination of the lever 11 and also control the motor 1 to move the X-ray imaging part 27 in the opposite direction.

In the normal mode 13a, X-rays are irradiated to get a X-ray image by pushing the X-ray switch 12. In this case, the CPU 8 controls the X-ray high voltage generator 41 to provide high voltage with the X-ray tube 5 and then the X-ray tube 5 irradiates X-rays.

In the imaging part moving mode 13b and the imaging part and table moving mode 13c, when the X-ray switch 12 is pushed, X-ray irradiation and radiography of the X-ray imaging part 27 starts and continues until the X-ray switch 12 is pushed again. Radiography can be carried out during movement of the X-ray imaging part 27 and/or the table 40 by further operating the lever 11.

Figure 3:
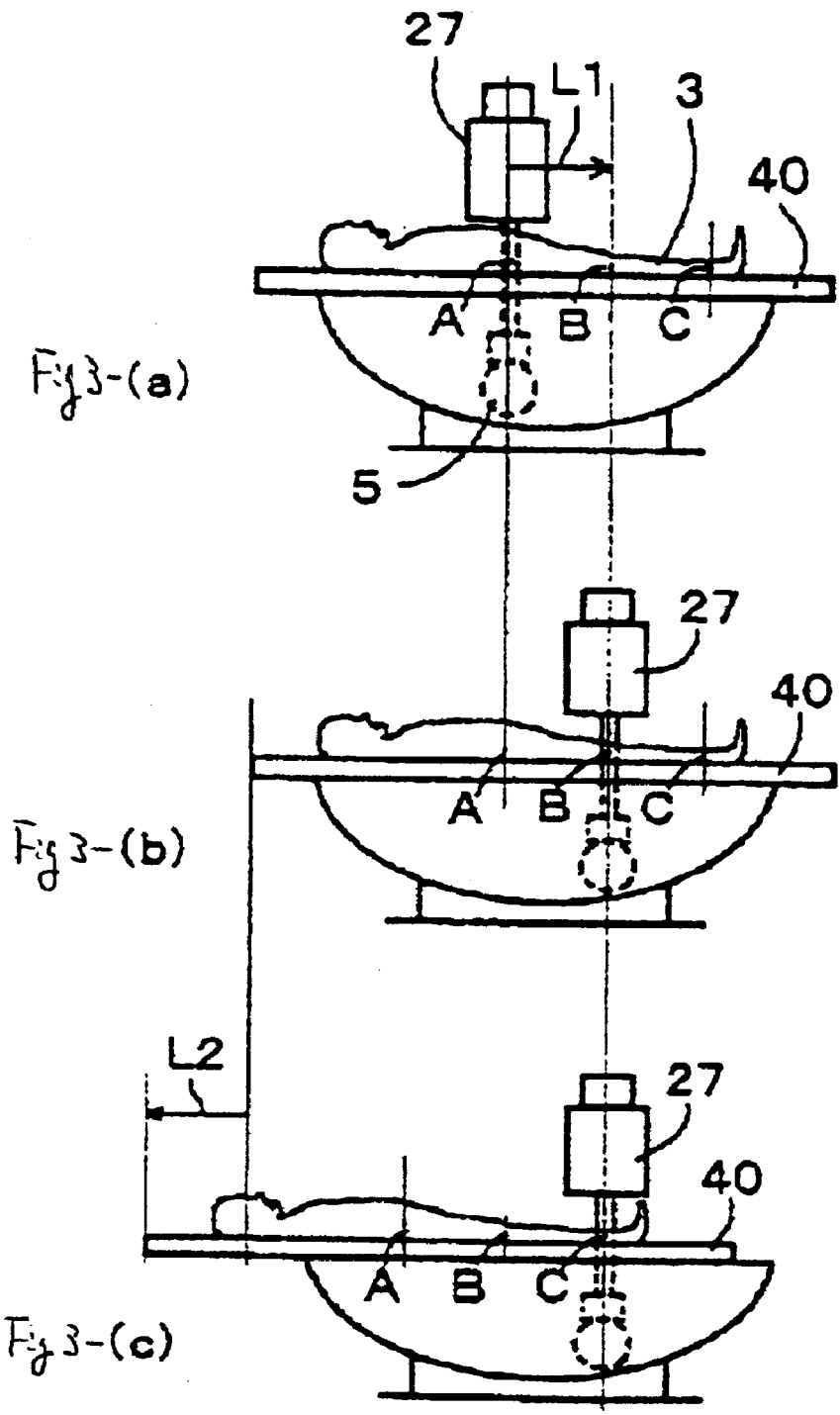
FIGS. 3(a), 3(b) and 3(c) are schematic views showing how the X-ray imaging part and the table may travel relatively.

FIG. 3(a), FIG. 3(b) and FIG. 3(c) show the relative position of the X-ray imaging part 27 and the table 40 with the person 3. In FIGS. 3(a), 3(b) and 3(c), the range of radiography in the legs is from point A to point C. The X-ray imaging part 27 is set at point A when radiography starts. When carrying out angiography of the legs in the imaging part and table moving mode 13c, a contrast medium injector, not shown in the Figures, is set in an artery of the abdomen. Then, the imaging part and table moving mode 13c is selected by operating the image mode selection switch 13 on the control part 22. When the X-ray switch 12 is pushed, X-ray irradiation starts and also the X-ray imaging part 27 starts radiography at the same time. In this condition, contrast medium is injected into the artery of the abdomen by activating the injector. The flow of a contrast medium in the vessel is shown on a monitor such as the monitor 46 in FIG. 4, not shown in the FIG. 1–3. The lever 11 is operated to chase the contrast medium's flow so that it is shown on the monitor. Relative speed of the table 40 to X-ray imaging part 27 can be adjusted by adjusting the amount of the inclination of the lever 11. When the X-ray imaging part 27 reaches the point C, operation of both of the X-ray switch 12 and the lever 11 is stopped and the X-ray imaging part 27 and the table 40 stop, then angiography is completed. In FIG. 3, through the above series of operation, the X-ray imaging part 27 travels for distance L1, from the point A to the point B, and also the table 40 travels for distance, L2 from the point C to the point B. Therefore, the range of angiography becomes the distance L1+L2, from the state shown in FIG. 3(a) to the state shown in FIG. 3(c).

Thus it is possible to move the X-ray imaging part 27 and the table 40, at the same time, in opposite directions from each other and also at the instructed speed, according to an instruction from a movement instruction means such as the lever 11. Therefore, the operator can easily have the X-ray imaging part 27 follow a contrasted blood flow in the body. Because the X-ray imaging part 27 and the table 40 move in opposite directions from each other, the apparatus can be downsized and installed in a small inspection room. In addition, the speed of table 40 may be reduced as compared to the prior art, while the speed of the X-ray imaging part 27 relative to the table 40 is still sufficient, thus making a person on the table feel more comfortable. Further, because one or more motors need only stop a body (either the X-ray imaging part 2 or table 40) which only needs to move at a speed half as fast as the prior art, the motors may need not be as powerful, and this may be less expensive.

It is emphasized that the above description is merely one detailed example. Modifications of this example will be apparent to those of ordinary skill which do not deviate from the spirit and scope of the invention. For example, although in the above embodiment CPU 8 controls motor and motor 2 via the imaging part velocity control circuit 7 and the table velocity control circuit 6, other systems may be used, such as an electronic circuit to control the motors without the CPU 8. For example, instead of a lever, the instruction means may be a track ball or a switching device. A lever which detects direction and amount of a pressure at which the operator grasps may also be used. The CPU 8 may use this detected direction and amount instead of the direction and the amount of the lever in the above embodiment to control the movement of the imaging part 27 and table 40.

In addition, while various aspects of the above detailed example have certain advantages, not all those aspects are intended to be a required element of the invention as it is most broadly defined. The spirit and scope of the invention is intended to be defined by the following claims.

What is claimed is:

1. An apparatus for X-ray fluoroscopy comprising:
   an imaging part operative to perform imaging and including an X-ray tube and an image intensifier, said tube being opposed to said intensifier;
   a table on which a person may lie for examination;
   a driver for moving said imaging part and said table;
   a user interface adapted for receiving instructions of direction and speed of said imaging part and table from an operator;
   a controller which controls said driver to move said imaging part and to move said table simultaneously and in opposite directions relative to each other according to the instructions received by said user interface wherein, simultaneous movement of said imaging part and the table occurs while the imaging part performs imaging, wherein said user interface includes a lever for generating signals of a motion direction and a motion speed of said imaging part and said table, said signal of said motion direction corresponding to an inclination direction of said lever and said signal of a motion speed corresponding to an inclination amount of said lever.

2. An apparatus for X-ray fluoroscopy according to claim 1, further comprising:

a monitor displaying an X-ray image in accordance with an output from said imaging part.

3. An apparatus for X-ray fluoroscopy according to claim 1, wherein the inclination direction of said lever corresponds to motion direction of said imaging part or table, and said controller controls said driver to move said imaging part or table in the direction of the inclination direction of said lever.

4. An apparatus for X-ray fluoroscopy according to claim 1, wherein said controller controls said driver to increase the speed of said imaging part and said table as the inclination amount of said lever increases.

5. An apparatus for X-ray fluoroscopy according to claim 1, wherein a lever is attached to said imaging part.

6. An apparatus for X-ray fluoroscopy according to claim 1, wherein said driver includes a first motor to drive said imaging part and a second motor to drive said table.

7. A method of angiography comprising the steps of:

placing an imaging part operative to perform imaging and including an X-ray table and an image intensifier at a target point of a subject person for starting angiography;

irradiating X-rays with said X-ray table;

injecting a contrast medium into the person;

moving the imaging part and moving a table on which the subject person lies simultaneously and in opposite directions relative to each other;

performing imaging while simultaneous movement of the imaging part and the table is occurring; and adjusting motion direction and speed of said imaging part and said table with a user interface having a lever, the lever operative for generating signals of a motion direction and a motion speed of said imaging part and said table, said signal of said motion direction corresponding to an inclination direction of said lever and said signal of a motion speed corresponding to an inclination amount of said lever.

8. The method of claim 7 further comprising:

watching a display of the X-ray image; and operating the user interface so that the imaging part follows the control medium.

9. An angiography of legs comprising steps of:

placing an imaging part operative to perform imaging and including an X-ray tube and an image intensifier at a target part of legs of a subject person for examination for starting angiography;

irradiating X-rays with said X-ray tube;

injecting contrast medium into the artery of the abdomen of the person;

moving the imaging part and moving a table on which the subject person lies simultaneously and in opposite directions relative to each other;

performing imaging while simultaneous movement of the imaging part and the table is occurring; and adjusting motion direction and speed of said imaging part and said table with a user interface having a lever, the lever operative for generating signals of a motion direction and a motion speed of said imaging part and said table, said signal of said motion direction corresponding to an inclination direction of said lever and said signal of a motion speed corresponding to an inclination amount of said lever.

10. The method of claim 9, further comprising:

watching a display of the X-ray image; and operating the user interface so that the imaging part follows the control medium.

11. The method of claim 10, further comprising:

stopping the irradiating of X-rays and movement of said imaging part and said table when the imaging part reaches the toe of said person.

12. An apparatus comprising:

imaging means for obtaining an X-ray image of a subject;

a table on which the subject may be placed;

driving means for driving the imaging means and the table;

a user interface adapted for receiving instructions of direction and speed of said imaging means and table from an operator; and control means for controlling the driving means to move said imaging means and to move said table simultaneously and in opposite directions relative to each other in response to the instructions received by said user interface, wherein simultaneous movement of said imaging means and the table occurs while the imaging means obtains an X-ray image of the subject, wherein said user interface includes a lever for generating signals of a motion direction and a motion speed of said imaging means and said table, said signal of said motion direction corresponding to an inclination direction of said lever and said signal of a motion speed corresponding to an inclination amount of said lever.

* * * * *